United States Patent [19]

Redding

[11] Patent Number: 4,558,602
[45] Date of Patent: Dec. 17, 1985

[54] LARGE CAPACITY SAMPLE BUCKET AND BUCKET SAMPLER HAVING LOW CLEARANCE

[76] Inventor: James A. Redding, 615 Washington Rd., Pittsburgh, Pa. 15228

[21] Appl. No.: 624,827

[22] Filed: Jun. 26, 1984

[51] Int. Cl.$^4$ .............................................. G01N 1/20
[52] U.S. Cl. .......................... 73/863.53; 73/863.56; 73/863.57; 73/863.01; 73/864.32; 220/334; 220/335; 198/509; 198/706; 198/713
[58] Field of Search ........... 73/863.53, 864.32, 863.01, 73/863.51, 863.52, 863.54, 863.55, 863.56, 863.57, 863.41, 864.31, 864.51, 864.91, 863.91, 863.92; 198/509, 703, 706, 713, 714; 294/68, 73; 220/335, 334

[56] References Cited

U.S. PATENT DOCUMENTS

| | | | |
|---|---|---|---|
| 1,008,996 | 11/1911 | St. Clair | 198/703 X |
| 1,455,723 | 5/1923 | Hall | 220/334 |
| 2,920,736 | 1/1960 | Kämäräinen | 198/509 |
| 3,373,615 | 3/1968 | Silver et al. | 73/863.53 |
| 3,376,752 | 4/1968 | Malone | 73/863.53 |
| 3,452,857 | 7/1969 | Stambera | 198/703 |
| 3,499,327 | 3/1970 | Lane, Jr. | 73/863.52 |
| 3,524,352 | 8/1970 | Paul | 73/863.53 |
| 3,683,702 | 8/1972 | O'Brien et al. | 73/863.52 |
| 3,791,218 | 2/1974 | Pennington | 73/864.32 |
| 4,345,697 | 8/1982 | Wilson et al. | 220/335 |

FOREIGN PATENT DOCUMENTS

| | | | |
|---|---|---|---|
| 1077461 | 3/1960 | Fed. Rep. of Germany | 73/863.53 |
| 26037 | 8/1970 | Japan | 73/863.53 |
| 820891 | 9/1959 | United Kingdom | 73/863.53 |
| 2077702 | 12/1981 | United Kingdom | 73/863.92 |
| 696336 | 11/1979 | U.S.S.R. | 73/863.51 |
| 848424 | 7/1981 | U.S.S.R. | 198/703 |

OTHER PUBLICATIONS

"High-Speed Sampling Cutters and Their Effect on Bias", J. Test & Eval. (USA); vol. 7, No. 6, pp. 338–343; Nov. 1979; W. V. Bluck et al.

*Primary Examiner*—Stewart J. Levy
*Assistant Examiner*—Tom Noland
*Attorney, Agent, or Firm*—Depaoli & O'Brien

[57] ABSTRACT

A sample bucket is disclosed for intercepting a sample while cutting through a flow of particulate material. The bucket is in the form of a receptacle having an open mouth and a suitable depth for retaining a desired gross sample without overflow thereof. The sample bucket has a top enclosure wall which narrows the mouth of the bucket, while the bucket is in its upright position, in order to prevent overflowing and which widens the mouth of the bucket, while the bucket is in its inverted position, to allow full discharge of the contents. The sample bucket is preferably used as a part of a bucket sampler comprising a pair of chain conveyors which pass over a conveyor drive assembly and a conveyor tail assembly having sprocket wheels with sprockets. The bucket sampler is attached near its upper end to the pair of chain conveyors which straddle it, but the bucket sampler is supported at a pivot point on opposing sides by pivotally attached wheels which ride upon a pair of plates while the bucket traverses back and forth in both inverted and upright positions. With reference to the upright position, the point of attachment to the chain conveyors is disposed above the pivot point so that the bucket occupies substantially less than twice its depth in both the inverted and upright positions. This feature causes the bucket sampler to be very satisfactory for retrofitting existing chemical and other process plants, such as coal fired electrical generating plants.

24 Claims, 11 Drawing Figures

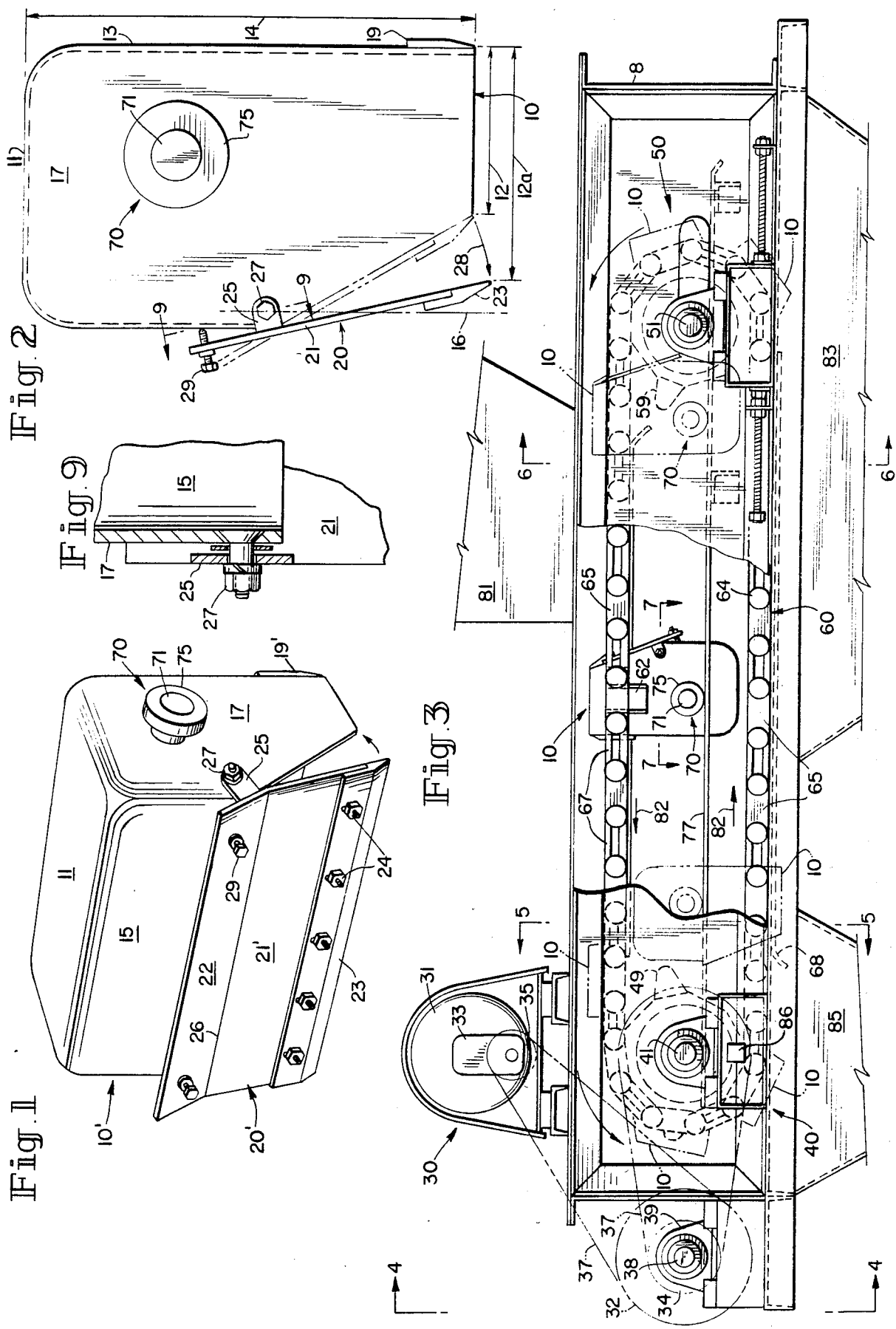

U.S. Patent Dec. 17, 1985 Sheet 3 of 4 4,558,602
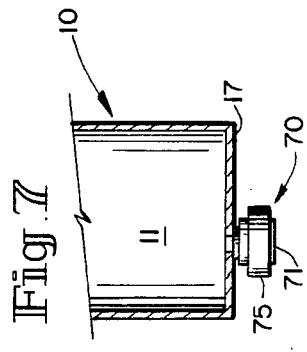
Fig. 7
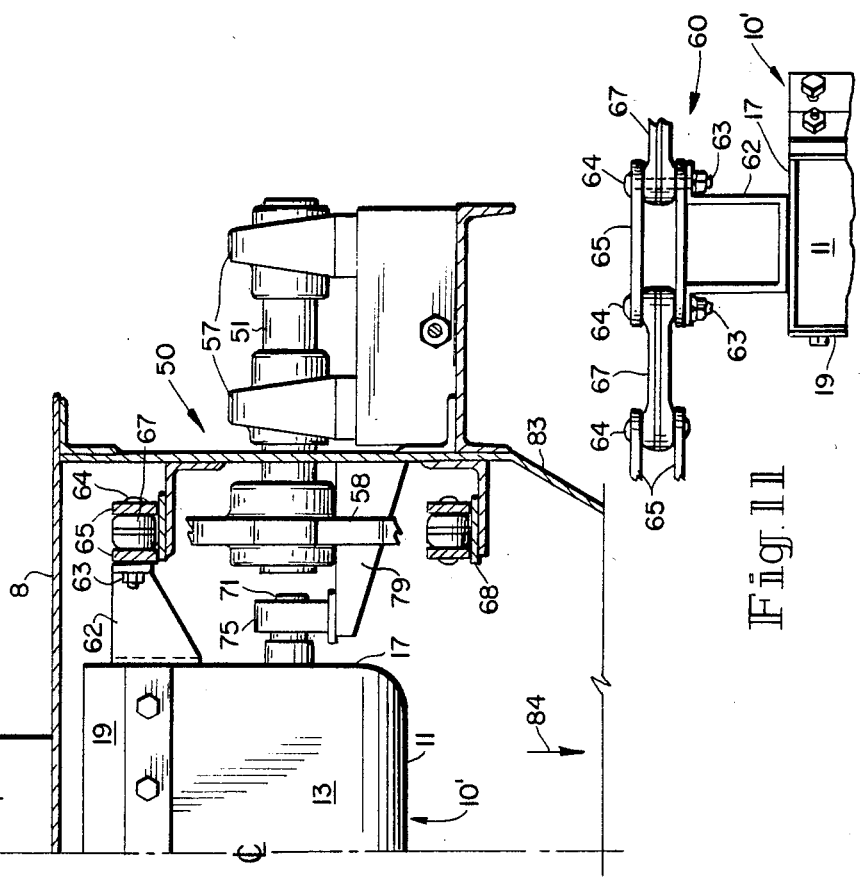
Fig. 6
Fig. 11
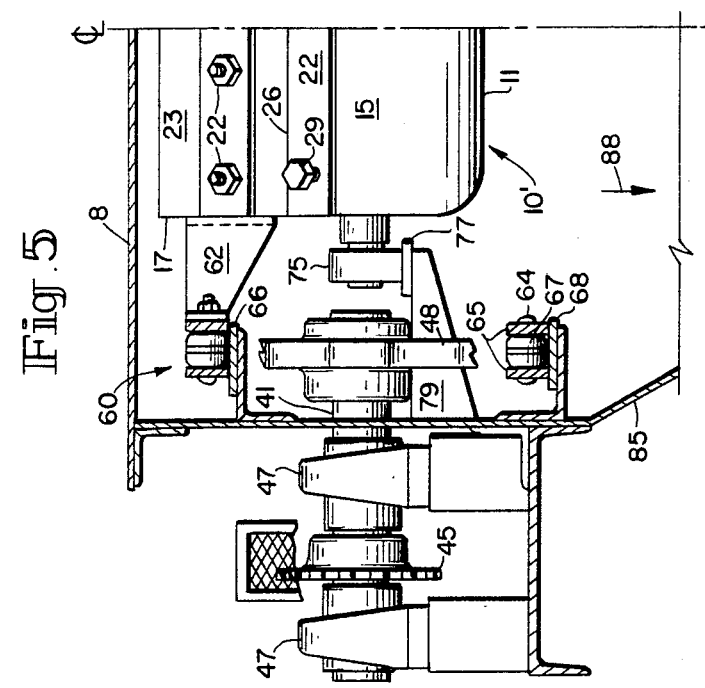
Fig. 5
Fig. 10

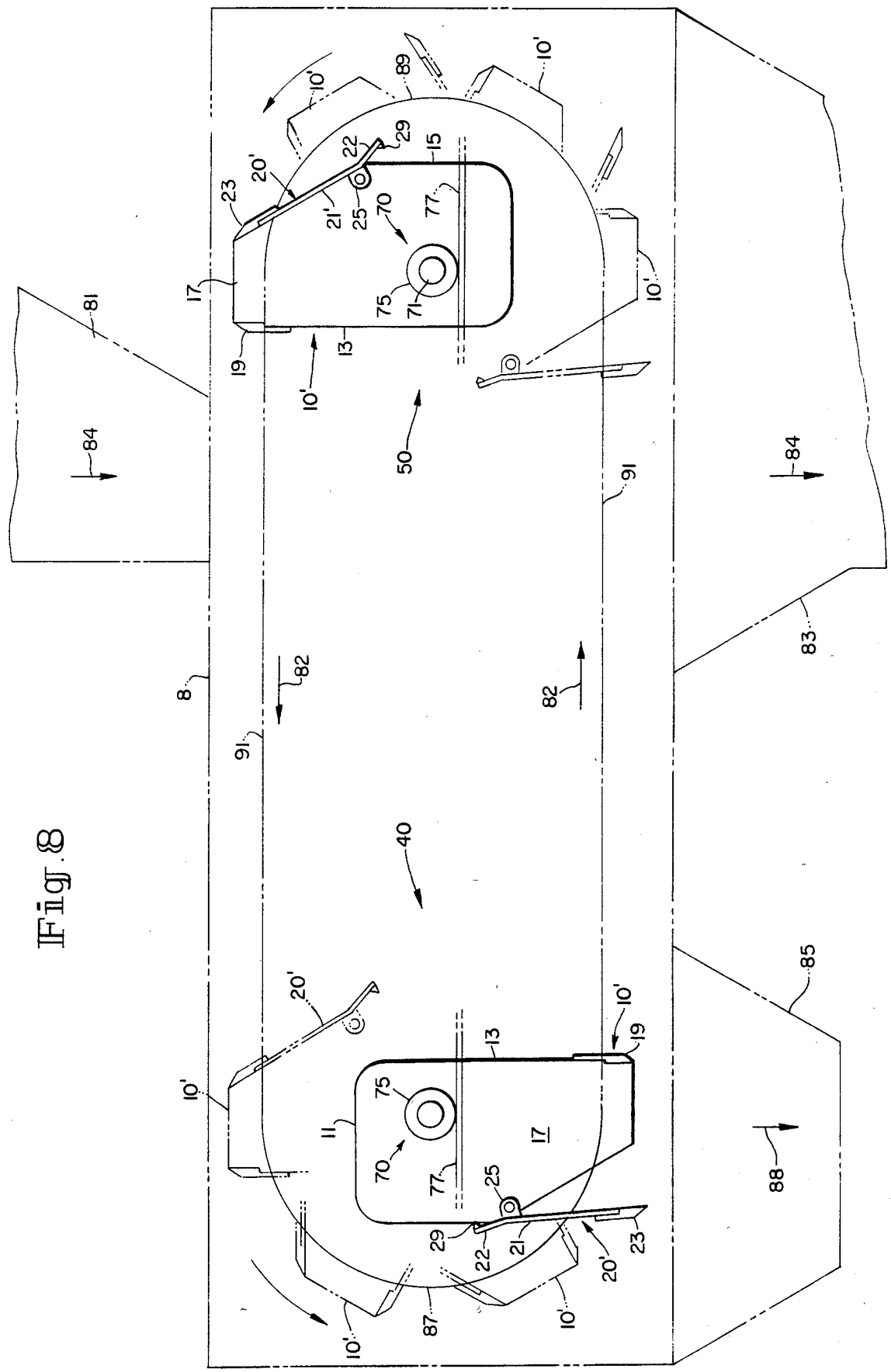

LARGE CAPACITY SAMPLE BUCKET AND BUCKET SAMPLER HAVING LOW CLEARANCE

BACKGROUND OF THE INVENTION

1. Field of the Invention

This invention relates to capture devices for sampling and particularly relates to traveling bucket devices for cutting across a falling stream of particulate material and intermittently capturing a sample thereof.

2. Review of the Prior Art

It has been necessary for many years to obtain reliable samples of particulate materials, such as grain, crushed rock, gravel, sand, ores, coals, particulate or pulverized chemicals, and like materials. In some instances such materials are wet or sticky, so that complete emptying of sampling buckets presents a challenge.

One of the most reliable methods of obtaining representative samples is to take a full cross-section cut from a moving stream of particulate material that is falling from one conveyor to another or from a conveyor to a hopper or bin, or the like. If the particulate material is heterogeneous, such as coal and many ores, collection and handling of samples that adequately represent the bulk lot being transferred requires the collection of increments that are proportional in weight to the flow and evenly distributed over the entire lot. In addition, the amount of some important impurities may determine the size of the sample and the frequency with which the sample is taken from the moving stream of material.

The frequency of the cut through a moving stream of material may be varied according to heterogeneity of the material, the amount of important impurities, the maximum size of the material and the like, but the more frequent the cut, the more representative the sample becomes. However, the amount of material taken from the cut and the frequency of the sampling interval are usually determined by the amount or volume of the material required for sample analysis, the size of the largest particles, the quantity required to produce unbiased results, and on-the-job experience.

With respect to sampling coal, it is equally as important for the seller of a coal as it is for the buyer thereof to know the moisture content, the ash content, and the like at the time and place of transfer from seller to buyer. Environmental regulations within recent years, particularly regarding coal fired electrical generating plants, have also required a reliable knowledge of the coal being burned, so that the coal must be sampled as it is delivered from the mine to the storage yard at the generating plants and from the storage piles to the bunkers that feed the boilers in order to control stack emissions. Moreover, the coal being burned within an electrical generating plant must be constantly sampled in order to maintain proper boiler efficiency.

Such sampling must be done not only in new coal fired generating plants but also in older existing plants which were not designed for coal sampling because it was not required at the time that they were built. Accordingly, coal sampling devices must be added to such older plants in order that they may meet environmental regulations. All such sampling must be done to conform to regulations of the American Society of Testing and Materials or according to some other regulation. For example, ASTM D-2234, entitled "Standard Methods for Collection of a Gross Sample of Coal" must often be followed.

In the past, engineers designed the conveying system with a minimal drop of the coal at transfer points from one conveyor to another or from a conveyor to a coal bunker. In any case, a minimal available height usually limits the addition of retrofit sampling equipment. In most cases, installing such sampling equipment has required a costly raising or lowering of conveyors in order to obtain the required height for installing a sampling device that could extract the required cuts (increments) from the coal flow. There is consequently a need for a sampling device having a minimum of height so that it can be inserted between conveyors or at the dumping point of a conveyor above a coal bunker without requiring a conveyor to be raised or lowered.

U.S. Pat. No. 946,744 discloses a belt conveyor, for conveying ore from one part of an ore treating plant to another, and a pair of sprocket chains which run beneath and beyond the upper end of the belt conveyor while carrying at least one bucket between them. The bucket has a trunnion at each end which is attached to a link of one of the chains and extends beyond the chains to a grooved trolley wheel which runs upon a track so that the bucket is supported at both ends. The bucket is inverted as it passes over a pair of sprocket wheels which carry the chains and dumps its contents into a box or truck.

U.S. Pat. No. 1,155,670 describes a sampling apparatus comprising a plurality of sampling buckets which are attached at the end thereof to a pair of chains that dump the buckets while passing over a pair of sprocket wheels at each end of the chains.

U.S. Pat. No. 1,423,890 describes a sampling apparatus comprising a belt type traveling conveyor having a plurality of openings therein and a sample hopper beneath the end of a discharge chute. All material leaving the chute, such as sand or grain, that falls upon the conveyor belt is carried to the end thereof and dumped into a hopper from which it may be delivered to any desired point. However, all material falling through the opening, as it passes by, drops into a sample hopper so that a desired increment of the falling material is obtained at desired intervals, depending upon the speed of the belt, the size of the openings, and the spacing therebetween.

U.S. Pat. No. 3,472,079 describes an automatic sampling system comprising a batch receiving structure which is disposed beneath the discharge end of the conveyor. The batch receiving structure has an outlet and an exit door and associated timing means for opening and closing the exit door, while stopping the conveyor, after a pre-determined amount has accumulated in the structure.

U.S. Pat. No. 3,524,352 relates to a material sampler which moves a sample bucket, having an adjustable opening, through a stream of falling aggregate at the offbear end of a belt conveyor. The bucket travels longitudinally beneath the belt conveyor and has a pair of stub shafts, attached to its opposite end walls, which are supported by bearing journals attached to a pair of carriage channel brackets supported by two pairs of carriage wheels which ride on a pair of track members. A disc is attached to the end of one stub shaft and has a plurality of projected pegs, which engage teeth in up-ending plates disposed at the ends of the track members, and a pair of peripheral edge notches, which are engaged by detente means for maintaining the bracket in an upright or upended position.

Some bulk materials that are required to be sampled, particularly coal, can be high in moisture content and thus rather sticky. The cutter opening width in the sample bucket is a function of the maximum size of the particles being sampled. The opening width is generally three times the maximum particle size. The quantity of sample that the bucket must hold is a function of the opening width, quantity of feed, and speed of the traveling bucket. The formula for determining this quantity, i.e., the pounds of material extracted per increment, is as follows:

increment, lbs. =

$$\frac{\text{(lbs./sec. of stream)} \times \text{(cutter opening width, in.)}}{\text{cutter speed, inches per second}}$$

When the bucket sampler is in its upside-down discharge position, this wet sticky material may not fully dump, particularly if the relation between the cutter opening width and the bucket width restricts the opening. Therefore, there is a need for a bucket that can aid in dumping wet, sticky material under such conditions.

SUMMARY OF THE INVENTION

It is accordingly an object of this invention to provide a sampling device requiring a minimum of height for retrofit installations.

It is another object to provide a sampling device that is reliable, durable, and capable of extracting a full-stream cut at selected intervals from a moving stream of particulate material, such as coal.

It is a further object to provide a sample bucket having sufficient height and width to contain the entire sample extracted from a given flow of particulate material without overflowing when cutting through the flow.

It is an additional object to provide a sample bucket that assures complete emptying of the bucket when inverted.

In accordance with these objectives and the principles of this invention, a low-clearance type bucket sampler and a sample bucket having means for preventing overflowing and for assuring complete emptying are provided. The sample bucket is made of suitable material for the application and has a top opening or mouth that is adequate to accommodate particulate material of various sizes, in accordance with ASTM requirements. The sample bucket has hardened lips in order to minimize maintenance. Furthermore, the bucket has a rounded bottom and a means for narrowing its top opening or mouth while being uprighted, in order to prevent overflowing, and for widening its top opening or mouth while being inverted, in order to assure complete emptying of the bucket.

The hinged top sample bucket can be combined with a wide variety of apparatuses and is useful for numerous applications. It can be used, for example, in bucket elevators or in bucket conveyors, such as for slurries that are nonpumpable or not easily pumped. In general, it can be used in any device in which material is gathered in a bucket and then dumped.

This sample bucket preferably comprises:
  A. four walls and a bottom which are mutually attached to form a receptacle having an open mouth and a depth, one wall being a partial wall which extends to a portion of the depth; and
  B. a hinged closure means which:
    (1) acts entirely by gravity,
    (2) extends beyond the partial wall toward the mouth,
    (3) selectively closes to restrict the size of the mouth while the sample bucket is in its upright position, and
    (4) selectively opens to enlarge the mouth while the sample bucket is in its inverted position.

The sample bucket is attached to and transported by a conveyor means. Preferably, the sample bucket is disposed between and attached to a pair of spaced-apart conveyors by an attachment means for attaching two walls of the bucket to the conveyors. This attachment means comprises a pair of brackets which are attached to two opposed walls of the four walls and to two links of the conveyor means, the partial wall being between the two opposed walls.

The sample bucket further comprises a support and pivot means for:
  A. supporting the sample bucket while it is reciprocally traversing a flow of material for selectively extracting a gross sample therefrom; and
  B. rotating the sample bucket between upright and inverted positions while enabling the sample bucket to require less than twice its depth for both the upright and inverted positions.

The support and pivot means comprises:
  A. a pair of trunnions which are attached to the two opposed walls; and
  B. a pair of wheels which are rotatably attached to the pair of trunnions.

The hinged closure means comprises:
  A. a top enclosure wall which:
    (1) extends beyond the top edge of the partial wall,
    (2) inclines inwardly to restrict the size of the mouth while the sample bucket is in its upright position, and
    (3) swings outwardly to increase the size of the mouth while the sample bucket is in its inverted position;
  B. a hinge means for hingeably supporting the top enclosure wall; and
  C. a stop means for selectively controlling its outward swinging.

As an alternative embodiment, the enclosure wall swings between the two opposed walls, and the stop means is a double stop means that controls both the inward and outward extents of swinging. Such a double stop means can comprise a lug, which is attached to and projects from the partial wall and has a bolt close to the wall and another bolt on its outer end, and a hole in the enclosure wall which surrounds the lug and is smaller than the bolts.

Preferably, however, each of the two opposed walls has a bevelled edge extending from the top edge of the partial wall, and the top enclosure wall extends sidewardly beyond the two opposed walls and rests upon the bevelled edges while the bucket is in its upright position.

The top enclosure wall has a cutter lip attached thereto alongside the mouth. This cutter lip is made of a very hard cast metal and is heavy in weight, compared to the weight of the metal of the top enclosure wall. The stop means is adjusted so that the top enclosure wall never opens beyond the point that its center of gravity is outside of the vertical line through the center of the hinge means. In addition, the rear or trailing wall may also be equipped with a similar cutter lip in order to minimize maintenance.

The bucket sampler comprises the sample bucket and a pair of conveyor means moving on both head and tail sprocket wheels that utilize snub shafts, thereby providing the minimum height needed for retrofit installations. The conveyor means can be cables, belts, chains, or the like, but chain conveyors, which are not subject to slippage, are preferred because maintaining the pair of belts in synchronization is mechanically essential and running at constant speed is essential for sampling. The reason therefor is that the quantity of sample gathered is a function of the speed of the bucket which must consequently remain constant throughout the sampling period. The conveyor means is preferably a pair of sampler chain conveyors and upper and lower support means therefor.

The sampler chain conveyors are preferably supported by replaceable wear bars as the upper and lower support means. A bucket support wheel is attached to each side of the bucket on the vertical center line thereof and is supported by a support track while the bucket is being driven in both directions, so that the sample bucket is straddled by a pair of support tracks while it moves back and forth.

The head and tail pulleys are drive and tail sprocket wheels which are driven by a common drive shaft assembly to assure that each of the two conveyor drive sprocket wheels are driven at exactly the same speed. The common drive shaft assembly is driven by a motor and reducer assembly of proper size in order to obtain the desired speed of the sample bucket as it passes through the downflow of particulate material. The entire bucket sampler is enclosed in a dust-tight enclosure.

The bucket sampler, used for obtaining gross samples from a flow of particulate material, comprises:
  A. a sample bucket in the form of a receptacle having a depth and an open mouth at its upper end when in the upright position and at its lower end when in the inverted position;
  B. a motor and drive assembly;
  C. a conveyor drive assembly;
  D. a conveyor tail assembly;
  E. a sampler conveyor means for conveying the sample bucket;
  F. a support frame;
  G. a bucket attachment assembly which attaches opposite sides of the bucket to the conveyor means, whereby the positions of attachment of the opposite sides to the conveyor means describe a pair of semicircular arcs, while passing over the conveyor drive assembly and the conveyor tail assembly, that have a diameter that is less than the depth; and,
  H. a support and pivot assembly which is attached to the sample bucket on its opposite sides between the positions of attachment to the conveyor means and the bottom of the bucket and which:
    (1) supports the sample bucket during its reciprocal traverse of the flow; and
    (2) enables the sample bucket to be rotated between its upright and inverted positions while enabling the sample bucket to require less than twice its depth for both the upright and inverted positions.

The motor and drive assembly comprises:
  A. a motor means, such as an electrical motor or a hydraulic motor;
  B. a motor reducer which is connected to the motor means;
  C. a drive shaft which is rotatably supported by the support frame; and
  D. a power assembly which transmits power from the motor reducer and to and from the drive shaft.

The conveyor drive assembly comprises:
  A. a pair of drive snub shafts which are rigidly supported by shaft bearings;
  B. a power transmittal means which is attached to the frame for receiving power from the drive shaft;
  C. a snub shaft bearing assembly which rigidly and rotatably supports the drive snub shafts; and
  D. a pair of chain drive sprocket wheels which are attached to the drive snub shafts.

The conveyor tail assembly comprises:
  A. a pair of take-up snub shafts;
  B. take-up shaft bearing assemblies which rotatably and rigidly support the take-up snub shafts; and
  C. a pair of sampler tail sprocket wheels.

The conveyor means comprises:
  A. a pair of sampler chain conveyors which revolve simultaneously and in parallel over the sprocket wheels of the conveyor drive assembly and of the conveyor tail assembly and between which the sample bucket is disposed, each chain conveyor comprising, in tensional connection, a plurality of pins, a plurality of roller link plates, and a plurality of pin link plates;
  B. a pair of upper sampler chain wear bars which support the pair of sampler chain conveyors in the upper reaches thereof; and
  C. a pair of lower sampler chain wear bars which support the pair of sampler chain conveyors in the lower reaches thereof.

Assuming that the sample bucket is located upside-down directly over the sample discharge, having been stopped there by a proximity switch, the sample bucket is next moved along the length of the support tracks, while upside down, upon actuation of the motor by a given signal, manual or remote, from a timer or other device. Upon reaching the tail sprocket wheels, the sample bucket uprights itself while its points of attachment to the chain conveyors describe semicircles around the tail sprockets. It promptly begins to intercept or cut through the continually falling flow of material that is passing through the feed inlet and extracts a quantity of this material while cutting through the falling stream. The top opening of the sample bucket totally encompasses the width of the feed inlet so that each and every piece of material passing through the feed opening to the feed discharge has an equal chance of reporting to the sample, thereby producing an acceptable sample in accordance with any regulation.

The sample bucket continues in the reverse direction until it reaches the pair of sample drive sprocket wheels and then proceeds to turn upside-down while its points of attachment to the chain conveyors again describe semicircles, thus emptying the extracted sample into a sample collection device while expanding its opening to a width equalling the interior width of the sample bucket. At this upside-down point, a proximity switch stops the motor, and the sample bucket comes to rest, awaiting the next starting signal.

As the sample bucket passes through the falling feed stream of particulate material, pieces thereof may be knocked forward onto the flat portion of the enclosure between the feed discharge and the sampler discharge.

Because the enclosure is designed with minimum clearance, the stray material that gathers on this flat portion of the enclosure is plowed back into the feed discharge by the sample bucket on its return movement while upside down. Thus a sample is extracted from a flow of material in accordance with published regulations while using a minimal height as a result of the snub shaft arrangement and centered support means on the sample bucket.

BRIEF DESCRIPTION OF THE DRAWINGS

The invention may be more fully understood by consideration of the following drawings in which like numbers are used for identifying each part of the invention.

FIG. 1 is a side perspective view of the sample bucket in its upside-down or inverted position and with its top enclosure wall in hingeably open position.

FIG. 2 is a side elevational view of a sample bucket, also in its upside-down position and with the top enclosure wall being shown in phantom at its closed position and in solid lines at its open position.

FIG. 3 is a front elevational view of the bucket sampler, with a portion of the enclosure being broken away to show the sample bucket midway on its upright horizontal travel and in loaded condition, and with two other phantom representations of the bucket being shown to illustrate other positions thereof.

FIG. 5 is a partial sectional view of the bucket sampler, taken in the direction of the arrows 5—5 in FIG. 3, that shows the sampler chain drive assembly and a portion of the sample bucket in its upright position.

FIG. 6 is a partial sectional view, taken in the direction of the arrows 6—6 in FIG. 3, that shows the sampler chain tail assembly and a portion of the sample bucket in its upright position.

FIG. 7 is a sectional top view, taken in the direction of the arrows 7—7 in FIG. 3, of the sample bucket along one side thereof to show one of the wheel assemblies for supporting the sample bucket on the bucket support wheel tracks.

FIG. 8 is a schematic side elevational view of the bucket sampler that shows the passage of the buckets in relation to the inlet and discharge chutes for the particulate material and the sampler discharge chute and which additionally shows the sampler bucket in its upside-down and open positions, while revolving around the tail sprockets and narrowing its opening or mouth and while pivoting around the drive sprockets and widening its opening or mouth, respectively.

FIG. 9 is a detailed sectional view, taken in the direction of the arrows 9—9 in FIG. 2, that illustrates the pivoting mechanism for the hinged top enclosure wall of the sample bucket.

FIG. 10 is a top and side perspective view of the attachment bracket which is attached to each side of the sample bucket and to one link of each sample chain conveyor.

FIG. 11 is a partial top view of one side of the bucket, one attachment bracket, and one of the chain conveyor links.

DETAILED DESCRIPTION OF THE PREFERRED EMBODIMENTS

Figure 4:
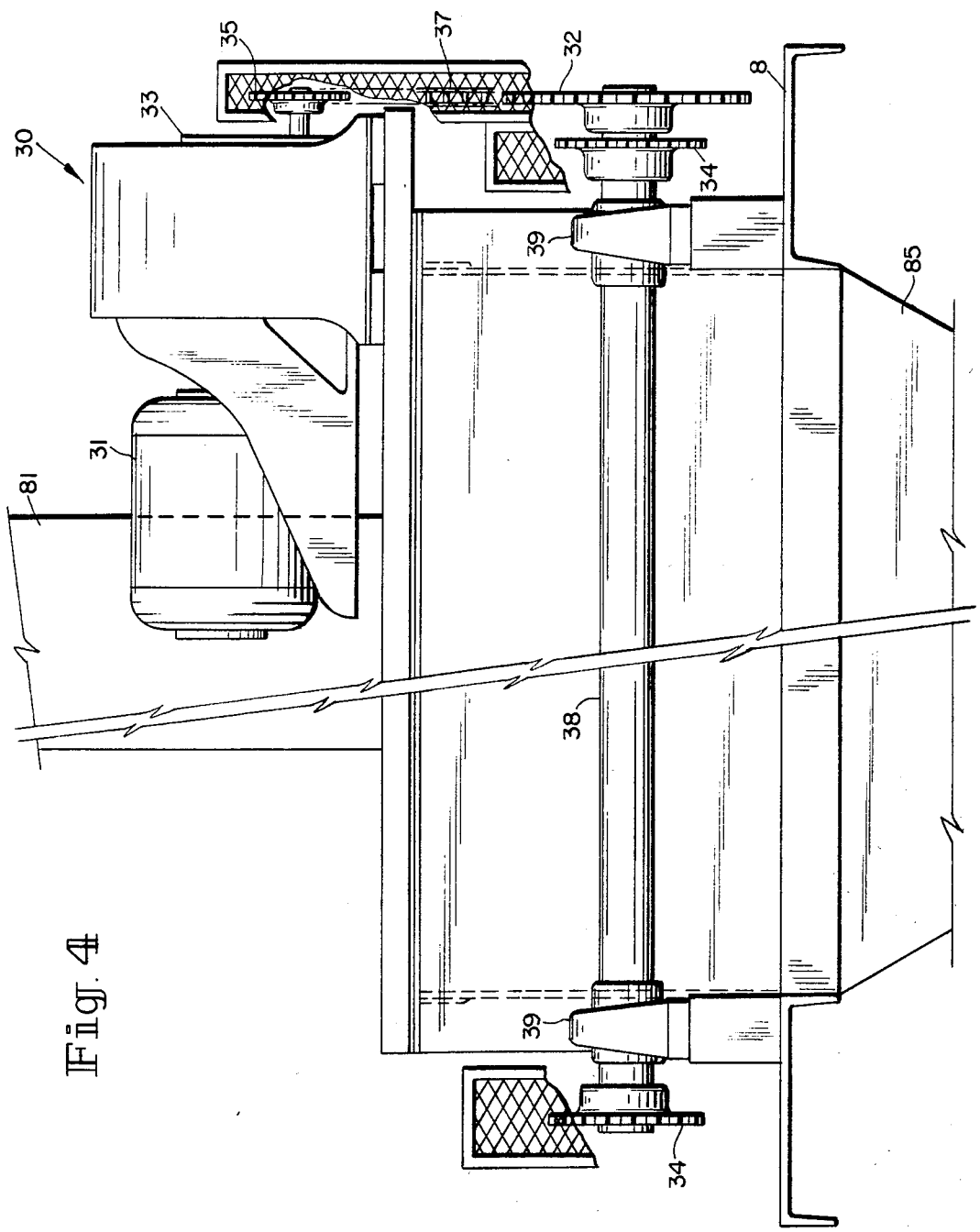
FIG. 4 is an end elevational view, taken in the direction of the arrows 4—4 in FIG. 3, that shows the motor and drive assembly of the bucket sampler.

As seen in FIGS. 1 and 2, sample buckets 10, 10' comprise a bottom 11, a leading or front wall 13 defining a depth 14, a partial trailing or rear wall 15, and a pair of opposed end or side walls 17 which define a mouth or opening of width 12 in upright position and width 12a in inverted position. The walls are rounded at edges and corners so that the bucket can empty as completely as possible. The same numbers are used for corresponding parts of buckets 10, 10' except that prime numbers are used for parts of bucket 10' that differ from corresponding parts of bucket 10.

Sample bucket 10 further comprises a hinged top enclosure wall assembly 20 in FIGS. 2 and 3. Wall assembly 20 in FIG. 2 comprises a wall 21 and a cutter lip 23 which is attached to the edge of wall 21 along the opening or mouth of the bucket. Enclosure wall 21 is attached to walls 17 by an attachment means, comprising a pair of lugs 25 and pair of nut and bolt assemblies 27. Wall assembly 20 swings open through angle 28, so that the mouth of the bucket widens from width 12 to width 12a, but it does not reach full vertical position because its swinging is controlled by a pair of stops 29.

Sample bucket 10', as the embodiment in FIG. 1, comprises a wall assembly 20' in FIGS. 1 and 8. Hinged top enclosure wall assembly 20' is exactly the same as wall assembly 20, except that it has a bent wall, the bend being along line 26 and separating a bent portion 22 from wall 21', and uses exterior bolts 24 for attaching its cutter lip 23 to wall 21'. Bend 26 in enclosure wall 21' enables wall 21' to be opened slightly further than wall 21, shown in FIGS. 2 and 3, without losing its capacity for being always able to return by gravity to its closed position.

Illustrated in FIG. 2 for bucket 10, this closed or gravity return position is defined with reference to vertical line 16 and applies to both embodiments 10, 10' shown in FIGS. 1 and 2; the centers of gravity of enclosure wall assemblies 20, 20' must not move beyond their respective vertical lines 16. This relationship is particularly effective as to bucket 10' because bent portion 22, separated from enclosure wall 21' by bend 26, causes the center of gravity of enclosure wall 20' to be closer to lip 23 than the center of gravity of enclosure wall 20. Opposed end or side walls 17 of bucket 10' also do not extend to the full depth 14 of walls 17 of bucket 10.

Referring to bucket 10 as the typical embodiment, cutter lips 19, 23, alongside the bucket opening or mouth, are usually made of a very hard cast metal because these lips traverse the downward flow of material and become definite points of wear on any sampling device. Lip 23 is recessed so that it covers the upper edge of enclosure wall 21 and completely protects it from wear and damage. Lips 19, 23 are also heavy in weight. It is particularly pertinent that lip 23 is heavy as compared to the weight of top enclosure wall 21 and thus acts as a counterweight on the end of wall 21 which is designed for vigorous widening of the bucket mouth to dump width 12a and equally vigorous narrowing to sampling width 12 which is designed to be thrice the maximum particle size.

When in its dump position, stops 29 prevent wall 21 from ever reaching a true vertical open position. The center of gravity of wall assembly 20 is thus always inward of vertical line 16. Therefore, upon the return of bucket 10 to its upright position, counter-weighted top enclosure wall 21 swings from its opened position, providing width 12a, to its closed position because of the force of gravity, thereby providing the required cutter opening width 12 for the next traverse of the downward flowing material, whereby bucket 20 extracts a selected quantity of particulate materials, such as coal, without overflowing.

The bucket sampler comprises a support frame and enclosure 8, a sample bucket 10, a motor and drive assembly 30, a conveyor drive assembly 40, a conveyor tail assembly 50, a sampler conveyor means 60 for conveying sample bucket 10, a support and pivot assembly 70, and an attachment means for attaching bucket 10 to conveyor means 60.

Motor and drive assembly 30 comprises a motor 31, a motor reducer 33 which is connected thereto, a reducer sprocket wheel 35, drive chains 37, a drive shaft 38, a follower sprocket wheel 32 and drive sprocket wheels 34 which are attached to shaft 38, and drive shaft bearing assemblies 39, as shown in FIGS. 3 and 4.

Conveyor drive assembly 40 comprises a pair of drive snub shafts 41, a pair of follower sprocket wheels 45, two pairs of bearing assemblies 47, and a pair of conveyor drive sprocket wheels 48 and sprockets 49 thereof, as shown in FIGS. 3 and 5.

Conveyor tail assembly 50 comprises a pair of take-up snub shafts 51, a pair of take-up shaft bearing assemblies 57, and a pair of sampler tail sprocket wheels 58 and sprockets 59 thereon, as shown in FIGS. 3 and 6.

Sampler conveyor means 60 comprises a pair of bucket support brackets 62 that are U-shaped and a pair of chain conveyors which each comprise a plurality of bracket bolts 63, pins 64, roller link plates 65, and pin link plates 67, as shown in FIGS. 3, 5, 6, 10, and 11. The sampler chain conveyors travel over a pair of upper sampler chain wear bars 66 and a pair of lower sampler chain wear bars 68, as shown in FIGS. 3, 5, and 6.

Support and pivot assemblies 70, as seen in FIGS. 3, 5, 6, and 7, each comprise a trunnion 71 which is attached to and projects from a side 17, a support wheel 75 which is rotatably mounted on a trunnion 71, a pair of bucket support wheel tracks 77 upon which wheels 75 roll back and forth, and track support brackets 79.

A suitable coal handling assembly, as shown in FIGS 3, 4, 5, 6, and 8, comprises a feed inlet chute 81, a feed discharge chute 83, and a sample discharge chute 85. The buckets travel in direction 82. The flowing particulate material, such as coal, travels through inlet chute 81 and discharge chute 83 in direction 84. The samples which are periodically discharged from bucket 10 travel in direction 88 while falling through discharge chute 85. Movement of bucket 10 is controlled by a proximity switch 86 which is best seen in FIG. 3.

Referring to FIG. 8, periodic movement of bucket 10, under control of proximity switch 86, is schematically illustrated with respect to its revolving around the drive assembly and the take-up or tail assembly. Around each assembly, bucket 10 is shown in four positions that illustrate how top enclosure wall 20' remains in open position until bucket 10' becomes nearly upright while going around tail or take-up assembly 50 and remains in closed position until within a few degrees of vertical while going around drive assembly 40.

FIG. 8 is particularly informative in that semicircular arc 87 shows the path of travel for the positions of attachment of bucket support brackets 62 on opposed sides 17 during discharge and because semicircular arc 89 shows the path of travel of this point of attachment during return to the upright position of bucket 10'. The positions of attachment essentially correspond with the centers of bracket bolts 63 and may be visualized in FIG. 8 as being the tangential intersection of arcs 87, 89 with lines 91 which represent the horizontal paths of travel of bolts 63 between drive and tail assemblies 40, 50. During both semicircular movements 87, 89, support wheels 75 continue to rest on wheel tracks 77 and simply reverse their direction of rotation as the bucket is carried in the reverse direction by chain conveyors 60 which are attached to bucket support brackets 62 on end walls 17 of buckets 10'. The movement of the sample bucket may also be explained by stating that support and pivot assembly 70 reciprocates while brackets 62 semi-revolve at the end of each horizontal movement 91.

While the foregoing embodiments are considered to be preferred, it is to be understood that numerous variations and modifications may be made in the method of this invention by those skilled in the art, and it is intended to cover in the appended claims all such variations and modifications as being within the true principles and scope of the invention.

What is claimed is:

1. A sample bucket for cutting through a flow of material and selectively extracting a gross sample therefrom in accordance with movement of a conveyor means, said bucket comprising:
   A. four walls and a bottom which are mutually attached to form a receptacle having an open mouth and a depth, one said wall being of less extent out from the bottom than the other three walls and is hereinafter called a partial wall, the depth being defined by the extent of the other three walls, said partial wall therefor extending only over a portion of said depth; and
   B. a hinged closure means which:
      (1) acts entirely by gravity,
      (2) extends beyond the top edge of said partial wall, the top edge being the edge of said partial wall that is opposite to the edge thereof that is adjacent to the bottom of the receptacle,
      (3) selectively closes to restrict the size of said mouth while said sample bucket is in said upright position, and
      (4) selectively opens to enlarge said mouth while said sample bucket is in said inverted position.

2. The sample bucket of claim 1 which further comprises a support and pivot means for:
   A. supporting said sample bucket while said bucket is reciprocally traversing said flow; and
   B. rotating said sample bucket between upright and inverted positions while enabling said sample bucket to require an amount of space having an extent that is less than twice said depth for both said upright and inverted positions.

3. The sample bucket of claim 2, wherein said support and pivot means comprises:
   A. a pair of trunnions which are attached to and project outwardly from two opposed walls of said four walls; and
   B. a pair of wheels, one said wheel being rotatably attached to one said trunnion.

4. The sample bucket of claim 3 which further comprises an attachment means for attaching said receptacle to a conveyor means, said attachment means comprising a pair of brackets which are attached to said two opposed walls and to said conveyor means, said partial wall being between said two opposed walls.

5. The sample bucket of claim 4, wherein said conveyor means comprises a pair of spaced-apart chain conveyors which are disposed in parallel and run at a constant speed, said sample bucket being disposed therebetween and attached to said conveyors by said attachment means.

6. The sample bucket of claim 5, wherein said attachment means reciprocates between semi-revolutions during which said hinged closure means alternately opens and closes.

7. The sample bucket of claim 1, wherein said hinged closure means comprises:
   A. a top enclosure wall which:
      (1) extends beyond the top edge of said partial wall,
      (2) inclines inwardly to restrict the size of said mouth while said sample bucket is in said upright position, and
      (3) swings outwardly to increase the size of said mouth while said sample bucket is in said inverted position;
   B. a hinge means for hingeably supporting said top enclosure wall; and
   C. a stop means for selectively controlling said swinging.

8. The sample bucket of claim 7, wherein said top enclosure wall swings between an opposing pair of the other three walls and said stop means controls both the inward and outward extents of said swinging.

9. The sample bucket of claim 7, wherein:
   A. each of said two opposed walls has a bevelled edge extending from said top edge of said partial wall; and
   B. said top enclosure wall has a width that is greater than that between the two opposed walls and therefore extends sidewardly beyond said two opposed walls and rests upon said bevelled edges while said bucket is in said upright position.

10. The sample bucket of claim 7, wherein said top enclosure wall has a cutter lip attached thereto alongside said mouth.

11. The sample bucket of claim 10, wherein said cutter lip is made of a very hard cast metal and is heavy in weight, compared to the weight of the metal of said top enclosure wall.

12. The sample bucket of claim 11, wherein said stop means is adjusted so that said top enclosure wall never opens beyond the point that its center of gravity is outside of a vertical line through the center of said hinge means.

13. The sample bucket of claim 12, wherein said top enclosure wall is bent outwardly near said hinge means and extends therebeyond.

14. The sample bucket of claim 13, wherein said top enclosure wall is attached to said two opposed walls by a pair of lugs and a nut and bolt assembly, these attachment elements functioning as said hinge means.

15. A bucket sampler for obtaining gross samples from a flow of particulate material, comprising:
   A. a sample bucket in the form of a receptacle having a depth, an open mouth, and a means for narrowing said mouth while being uprighted, in order to prevent overflowing, and for widening said mouth while being inverted, in order to assure complete emptying of said bucket;
   B. a motor and drive assembly;
   C. a conveyor drive assembly;
   D. a conveyor tail assembly;
   E. a sampler conveyor means;
   F. a support frame;
   G. a bucket attachment assembly which attaches opposite sides of said bucket to said sampler conveyor means, whereby the positions of attachment of said opposite sides to said sampler conveyor means describe semicircular arcs while passing over said conveyor drive assembly and said conveyor tail assembly, said arcs having a diameter that is less than said depth; and
   H. a support and pivot assembly which is attached to said sample bucket on said opposite sides between each said position of attachment and the bottom of said bucket and which:
      (1) supports said sample bucket during reciprocal traverse of said flow, and
      (2) enables said sample bucket to be rotated between said upright and inverted positions, while said positions of attachment describe said semicircular arcs, so that said sample bucket requires an amount of space having an extent that is less than twice said depth for both said upright and inverted positions.

16. The bucket sampler of claim 15, wherein said motor and drive assembly comprises:
   A. an electrical motor;
   B. a motor reducer which is connected to said motor;
   C. a drive shaft which is rotatably supported by said support frame; and
   D. a power assembly which transmits power from said motor reducer and to and from said drive shaft.

17. The bucket sampler of claim 16, wherein said conveyor drive assembly comprises:
   A. a pair of drive snub shafts;
   B. a power transmittal means which is attached to said frame for receiving power from said drive shaft;
   C. snub shaft bearing assemblies which rigidly and rotatably support said drive snub shafts; and
   D. a pair of chain drive sprocket wheels which are attached to said drive snub shafts.

18. The bucket sampler of claim 17, wherein said conveyor tail assembly comprises:
   A. a pair of take-up snub shafts;
   B. take-up shaft bearing assemblies which rotatably and rigidly support said take-up snub shafts; and
   C. a pair of sampler tail sprocket wheels which are attached to said take-up snub shafts.

19. The bucket sampler of claim 18, wherein said sampler conveyor means comprises a cable conveyor.

20. The bucket sampler of claim 18, wherein said sampler conveyor means comprises a chain conveyor.

21. The bucket sampler of claim 20, wherein said sampler conveyor means comprises:
   A. a pair of chain conveyors which revolve simultaneously and in parallel over said sprocket wheels of said conveyor chain drive assembly and of said conveyor tail assembly and between which said sample bucket is disposed, each comprising, in tensional connection, a purality of roller link plates, a plurality of pin link plates, and a plurality of pins;
   B. a pair of upper sampler chain wear bars which support said pair of sampler chain conveyors in the upper reaches thereof; and
   C. a pair of lower sampler chain wear bars which support said pair of sampler chain conveyors in the lower reaches thereof.

22. The bucket sampler of claim 18, wherein said flow is cut by said sample bucket immediately after being inverted into said upright position while passing over said conveyor tail assembly.

23. The bucket sampler of claim 22, wherein said sample bucket discharges its intercepted contents immediately after being inverted while passing over said conveyor drive assembly and discharges into a feed discharge chute.

24. The bucket sampler of claim 23, wherein said sample bucket is stopped by a proximity switch after discharging said contents and awaits a starting signal from a timer before resuming travel towards said conveyor tail assembly.

* * * * *